(12) United States Patent
Tarro

(10) Patent No.: US 6,222,010 B1
(45) Date of Patent: Apr. 24, 2001

(54) UROGENITAL CARCINOMA TLP PEPTIDES

(75) Inventor: Giulio Tarro, Rome (IT)

(73) Assignee: Unihart Corporation, Dublin (IE)

( * ) Notice: Subject to any disclaimer, the term of this patent is extended or adjusted under 35 U.S.C. 154(b) by 0 days.

(21) Appl. No.: 09/051,357

(22) PCT Filed: Jul. 2, 1997

(86) PCT No.: PCT/IT97/00158

§ 371 Date: Apr. 15, 1999

§ 102(e) Date: Apr. 15, 1999

(87) PCT Pub. No.: WO98/01462

PCT Pub. Date: Jan. 15, 1998

(30) Foreign Application Priority Data

Jul. 10, 1996 (IT) ............................................. RM96A0496

(51) Int. Cl.[7] .......................... A61K 38/00; C07K 14/00; C07K 16/00; C07K 17/00; C07K 2/00
(52) U.S. Cl. ...................... 530/300; 530/328; 424/277.1
(58) Field of Search ....................... 424/277.1; 530/300, 530/320

(56) References Cited

FOREIGN PATENT DOCUMENTS 0283443  2/1988  (EP) .
9401458  1/1994  (WO) .

OTHER PUBLICATIONS

"Human Tumor Antigens Inducing in vivo Delayed Hypersensitivity and in vitro Mitogenic Activity" by Tarro et al; Oncology; vol. 40, 1983, pp. 248–254, XP002045904 cited in the application–see the whole document.

"A New Tumor Associated Antigen of Non–Small Cell Lung Cancer: Tumor Libarated Proteins—A Possible New Tumor Marker" Garaci et al.; Anticancer Research, vol. 16, 1996, pp. 2253–2256, XP002045905, See p. 2253, col. 2, line 24–line 32.

"Antigenic Regions of Tumor Libarated Protein (TLP Complexes and Antibodies Against the Same" Tarro et al.; Biomedicine and Pharmacotherapy, vol. 47, Dec. 1993, p. 290, XP002046354, See Abstract.

*Primary Examiner*—Anthony C. Caputa
*Assistant Examiner*—Jennifer Nichols

(57) ABSTRACT

It is described a peptide consisting of a specific urogential carcinoma TLP epitope, wherein the TLP comprises the amino acid sequence GlyProProGluValGlnAsnAlaAsn. Also described are reagents to detect said urogenital TLP and pharmaceutical compositions.

2 Claims, No Drawings

SEQUENCE LISTING

<160> NUMBER OF SEQ ID NOS: 1

<210> SEQ ID NO 1
<211> LENGTH: 9

```
<212> TYPE: PRT
<213> ORGANISM: Homo Sapiens

<400> SEQUENCE: 1

Gly Pro Pro Glu Val Gln Asn Ala Asn
 1               5
```

UROGENITAL CARCINOMA TLP PEPTIDES

The present invention concerns peptides of the TLP complex (tumour released proteins) isolated from urogenital carcinoma.

In particular the invention refers to peptides of TLP protein complexes from human urogenital carcinoma having antigenic activity and to antibodies able to react with them, to be used in diagnostics and clinics.

TLP complexes are protein complexes which are present in human tumor cells. Among TLP proteins a 214 KDa protein is described (Tarro G., Oncology 40, 248–253, 1983). TLP are isolated from tumor tissues as described in the European Patent EP 283443. Italian Patent Application No. RM92A000506 identifies a TLP protein from lung carcinoma. The author of the instant invention has surprisingly found that TLP from urogenital carcinoma comprise new peptides having sequences which differ from known TLP peptides.

Therefore there is the need to identify TLP peptides, acting as epitopes, from urogenital carcinoma, to produce specific reagents, as antibodies.

The author of the instant invention has identified a peptide having a sequence comprised in the sequence of the 214 kDa TLP protein from either cervix, uterus, or testis adenocarcinoma, and from kidney neoplasia.

Therefore it is an object of the instant invention a peptide comprising a specific urogenital carcinoma TLP epitope, wherein said TLP is characterised by comprising the aminoacid sequence of SEQ ID No. 1:

GlyProProGluValGlnAsnAlaAsn.

According to a preferred embodiment the peptide comprises the aminoacid sequence of SEQ ID No. 1.

Further objects of the invention are specific reagents able to recognise the TLP from urogenital carcinoma, preferably said reagents comprise TLP antibodies. More preferably said antibodies recognise the peptide fragment having the sequence of SEQ ID No. 1.

Further objects of the invention are diagnostic kits to identify TLP from a sample comprising as specific reagents the antibodies of the invention.

Another object of the invention is a pharmaceutical composition comprising as active agent the peptide of the invention.

The invention will now be described according to exemplificating but not limiting examples.

EXAMPLE 1

Preparation of Tumoral Extract

A tumor biopsy of 12,55 g, from a 45 old woman having a cervix carcinoma, was thawed at room temperature and necrotic tissues were surgically removed. When the material resulted to be homogeneous, many washings were performed with Tris 1x (10 mM Tris-HCl pH 7.2) and the tissue subjected to three freeze-thawing cycles.

Used Tris washing solution was collected and centrifuged at 33,000 rpm for 1 hr. The supernatant was collected and frozen.

The tissue was sonicated three times for three min. and subsequently ultracentrifuged at 33,000 rpm for 120 min. The supernatant (5,7 ml) was collected, filtered on Agrodisc filters (0.45 $\mu$m), and the tissue was suspended to a ratio of 1 g/ml Tris, and ultracentrifuged at 33,000 rpm for 60 min. The supernatant (0.5 ml) was filtered and added to the previous one.

The same process was performed on either testicular carcinoma (total yield 1.9 ml) or kidney neoplasia samples.

EXAMPLE 2

Identification of Peptides Comprised in the TLP Protein from Urogenital Carcinoma The TLP complex is isolated from urogenital carcinoma extracts as described in the EP 283443 patent. Samples utilised are:

1) cervix adenocarcinoma;
2) testicular carcinoma;
3) kidney neoplasia.

The protein content resulted to be as follows:

TABLE 1

| Sample | Total mg | mg/ml TLP |
|---|---|---|
| cervix adenocarcinoma | 59.5 | 9.6 |
| testicular carcinoma | 7.4 | 3.9 |
| kidney neoplasia | 7.4* | 1.5 |

*Total kidney protein concentration did not allow an efficient TLP purification yield.

The TLP identification was performed through molecular weight determination (214 kDa) by means of denaturing electrophoretic analysis (SDS).

The removal of the main part of contaminants was performed by taking off gel sections corresponding to an apparent molecular weight of 214 kDa and by further electroeluting with a microelectroelution apparatus (AMICON).

Subsequently the TLP purity was confirmed by denaturing electrophoresis analysis. TLP was then transferred onto a PVDF (polyvinylidifluoride) membrane with an high protein capturing activity, and a sequential aminoacid analysis according to the Edman method was performed, with a protein automated sequencing apparatus by Applied Biosystems.

The aminoacid sequence which was found in all of samples was the following: GlyProProGluValGlnAsnAlaAsn (SEQ ID No.1).

What is claimed is:

1. A peptide consisting of the sequence set forth as SEQ ID NO:1.

2. A composition comprising the peptide of claim 1 and a carrier.

* * * * *